United States Patent [19]

Tungler et al.

[11] 4,299,992
[45] Nov. 10, 1981

[54] PROCESS FOR THE SELECTIVE HYDROXYMETHYLATION OF NITROTOLUENES

[75] Inventors: Antal Tungler; Tibor Máthé; József Petró; Zoltán Bende, all of Budapest, Hungary

[73] Assignees: Reanal Finomvegyszergyar; Budapesti Muszaki Egyetem, both of Budapest, Hungary

[21] Appl. No.: 151,597

[22] Filed: May 20, 1980

[30] Foreign Application Priority Data

May 29, 1979 [HU] Hungary ............................. RE 648

[51] Int. Cl.³ ........................ C07C 29/38; C07C 41/18
[52] U.S. Cl. .................................... 568/587; 568/705
[58] Field of Search ................................ 568/705, 587

[56] References Cited

U.S. PATENT DOCUMENTS 3,405,183 10/1968 Farrissey et al. ................. 568/705 X

FOREIGN PATENT DOCUMENTS 1568656 4/1969 France .

OTHER PUBLICATIONS

Bakke, Acta Chem. Scand., vol. 21 (1967) pp. 1967–1968.
Bakke, Acta Chem. Scand., vol. 23 (1969) pp. 3055–3061.

Primary Examiner—Bernard Helfin
Attorney, Agent, or Firm—Young & Thompson

[57] ABSTRACT

The invention relates to a new process for the selective hydroxymethylation of substituted ortho- or paranitrotoluenes of the general formula (I)

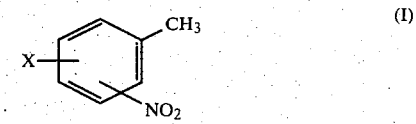

in order to prepare nitrophenylalkanols of the general formula (II)

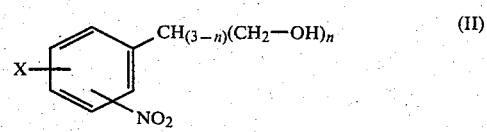

In the above formulae the nitro group is attached to the benzene ring in ortho or para position related to the methyl group or the hydroxyalkyl side chain, respectively, X stands for hydrogen, fluorine or an alkyl, alkoxy or nitro group, and n is 1, 2 or 3.

According to the process of the invention the starting substance is hydroxymethylated with an excess of formaldehyde at a temperature above room temperature in dimethyl formamide and in the presence of a strong base. The reaction is performed in dimethyl formamide containing 0.1 to 1% by weight of water, and the reaction is directed to the formation of the required end-product by properly adjusting the temperature and the amount of formaldehyde and the base with respect to the starting compound of the general formula (I).

In this way the required end-products can be prepared selectively also on an industrial scale.

4 Claims, No Drawings

PROCESS FOR THE SELECTIVE HYDROXYMETHYLATION OF NITROTOLUENES

The invention relates to a new process for the selective hydroxymethylation of substituted ortho- or paranitrotoluenes of the general formula (I)

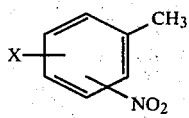

in order to prepare nitrophenylalkanols of the general formula (II)

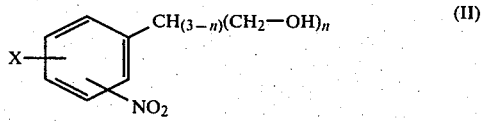

In the above formulae the nitro group is attached to the benzene ring in ortho or para position related to the methyl group or the hydroxyalkyl side chain, respectively, X stands for hydrogen, fluorine or an alkyl, alkoxy or nitro group, and n is 1, 2 or 3.

Preferred representatives of the alkyl and alkoxy groups are those containing a straight-chained or branched hydrocarbyl group of 1 to 6 carbon atoms.

It is known that ortho- and paranitrotoluenes can be hydroxymethylated with formaldehyde in the presence of a sodium or potassium alcoholate catalyst, in an aprotic solvent with high dielectric constant (Jan Bakke: Acta Chem. Scand. 1967, p. 1967). The reaction is performed with a 5 mol./l. solution of ortho-nitrotoluene in anhydrous dimethyl sulfoxide, and 5 mol % of sodium ethoxide are applied as catalyst in ethanol solution. A disadvantage of the method is that it provides the aimed compound with low yield (ca. 20 to 25%), furthermore the selectivity of the reaction is unsatisfactory. In this process compounds containing more hydroxymethyl groups are also formed in substantial amounts beside the desired nitrophenylethanol, and the selectivity of the reaction does not exceed 60%. (Selectivity is the molar ratio of the starting compound converted into the desired end-product to the starting compound converted in the reaction.) This known method cannot be applied on an industrial scale, since it is difficult to separate the individual components of the reaction mixture and to isolate nitrophenylethanol. From industrial aspects it is also very disadvantageous that the reaction proceeds with a satisfactory rate only if carried out in dimethyl sulfoxide or dimethyl formamide distilled from calcium hydride.

According to the reference cited above only those aldehydes can be reacted and under such conditions, for which the Cannizzaro reaction of the aldehyde is not competing with hydroxymethylation.

Another method of hydroxymethylation is disclosed in the published Japanese patent application No. 77-108,941. According to this method 2-(nitroaryl)-ethanols or 4-nitroaryl-ethanols are prepared from ortho- or paranitroalkylbenzenes by reacting them with an aldehyde in an aprotic polar solvent, in the presence of an alkali phenolate. According to a further method known in the art, nitrotoluenes are reacted with formaldehyde in the presence of a quaternary ammonium base to obtain nitrophenylethanols (published Japanese patent application No. 77-139,035). Another known method for the preparation of ortho-nitrophenylethanol is to react ortho-nitrotoluene with formaldehyde at a temperature of 50° to 130° C., in an aprotic polar solvent in the presence of an alkali hydroxide (published Japanese patent application No. 77-122,330).

These latter three methods attempt to increase the selectivity of the reaction by applying formaldehyde in a relatively low molar ratio as related to the starting substance (molar ratio of about 1:0.4). This really increases the selectivity of the reaction somewhat, but the yield of the end-product remains low, as a consequence of the lower amounts of formaldehyde applied.

It is also known to prepare nitrophenylethanols from nitrotoluenes by reacting the latter with an aldehyde and with a complex of a macrocyclic polyether formed with an alkali metal base (published Japanese patent application No. 77-156,825). The selectivity and the yield of this latter process, too, are unsatisfactory, and the method is difficult to apply on an industrial scale, owing to the complicated processing of the reaction mixture.

The invention aims at the elaboration of a new method for preparing alcohols of the general formula (II) from the respective nitrotoluenes with high yields and selectivity, using simpler technique and faster reaction than those known before.

It has been found that nitrotoluenes can be hydroxymethylated selectively with paraformaldehyde, if the reaction is performed in dimethyl formamide containing a small amount of water, in the presence of a strong base. It has also been observed that at temperatures exceeding room temperature hydroxymethylation can be made selective by the proper adjustment or programming of the amounts of formaldehyde and the base and the temperature conditions. Thus the required mono-, bis- or tris-methylol compound can be prepared selectively.

Based on the above recognitions, the invention relates to a new process for the preparation of nitrophenylalcohols of the general formula (II), wherein X and n are as defined above, by the selective hydroxymethylation of an ortho- or para-nitrotoluene of the general formula (I), wherein X is as defined above, with an excess of formaldehyde at a temperature above room temperature in dimethyl formamide and in the presence of a strong base. According to the invention, the reaction is performed in dimethyl formamide containing 0.1 to 1% by weight of water, and the reaction is directed to the formation of the required end-product by properly adjusting the temperature and the amount of formaldehyde and the base with respect to the starting compound of the general formula (I).

As strong base, preferably potassium hydroxide, sodium hydroxide or a quaternary ammonium base is used.

Without restricting the scope of the invention by strict kinetical interpretations, it should be noted that the high selectivity of the reaction can be attributed presumably to the fact that the ratios of the hydroxymethylation and the Cannizzaro reaction rates can be modified by the proper adjustment or timing of the temperature. Thus the reaction can be halted at the formation of the desired hydroxymethylated compound, since the formic acid formed in the Cannizzaro reaction neutralizes the base. The control of the molar ratio of formaldehyde alone is insufficient to increase the selectivity of the reaction, since with the consumption of formaldehyde in the reaction, the remaining strong base tarryfies the nitrotoluenes. It should also be noted that our experiences indicate that under identical conditions nitrophenylethanols are hydroxymethylated faster than nitrotoluenes. This explains why the products obtained in the conventional methods contain a relatively low amount of nitrophenylethanol. The temperature of the reaction is selected in accordance with the structure of the end-product to be obtained. The reaction temperature may vary between 30° C. and 150° C., within this range the interval of 60° to 100° C. is preferred to prepare monomethylol derivatives, whereas the bis- and tris-methylol compounds are prepared preferably at temperatures of 30° to 60° C. and 30° to 40° C., respectively.

Preferred conditions of the process according to the invention are as follows:

For the preparation of a monomethylol compound 1 mole of a starting substance of the general formula (I) is reacted with 1.5 to 2.2 moles of formaldehyde and 0.6 to 0.7 moles of a strong base at temperatures above 60° C.; for the preparation of a bis-methylol derivative 1 mole of a starting substance of the general formula (I) is reacted with 3 to 4 moles of formaldehyde and 0.5 to 0.6 moles of a strong base, and the temperature of the reaction mixture is maintained at 30° to 35° C. for at least one hour and thereafter at 50° to 60° C. until the reaction terminates; whereas for the preparation of a tris-methylol derivative 1 mole of a starting substance of the general formula (I) is reacted with at least 3 moles of formaldehyde and at most 0.1 moles of a strong base at temperatures below 40° C.

Formaldehyde is used preferably in the form of paraformaldehyde.

The main advantage of the process according to the invention is that it enables one to prepare alkanols of the general formula (II) from the respective nitrotoluenes of the general formula (I) with good yields and high selectivity.

A further advantage of the new process is that the reaction time is much shorter than that of the conventional methods. Thus e.g. when monomethylol compounds are to be prepared, the reaction time is shorter by about two orders of magnitude than in the conventional processes. This involves a proportional increase in productivity in the industrial processes.

With regard to industrial application, a significant advantage of the new method is that anhydrous solvent is not required. On the contrary, as has been pointed out, the presence of a small amount of water is necessary for the process of the invention. Thus the new process can be performed by utilizing dimethyl formamide of technical quality. Bases, such as sodium hydroxide or potassium hydroxide utilized in the new process, may also be of technical quality.

Since the non-reacted starting substance can be recovered from the reaction mixture, the new process is very economical on an industrial scale.

The invention is elucidated in detail by the aid of the following non-limiting Examples.

EXAMPLE 1

A mixture of 137 g (1 mole) of o-nitrotoluene, 60 g of paraformaldehyde and 400 ml of dimethyl formamide containing 0.5% by weight of water is heated to 70° C. under stirring. Thereafter 40 g of potassium hydroxide, covered with 100 ml dimethyl formamide, are added to the mixture at such a rate that the temperature of the reaction mixture does not increase above 120° C. The resulting mixture is stirred for 3 minutes at a temperature above 85° C., thereafter it is cooled and filtered through a sintered glass filter. The filtrate is acidified with hydrochloric acid to pH=3, filtered again, and the resulting filtrate is evaporated. 100 g of a residue, containing 80% by weight of 2-(o-nitrophenyl)-ethanol, are obtained. This residue is distilled in vacuo to obtain 70 g of 2-(o-nitrophenyl)-ethanol with a purity grade of 98%. 45 g of o-nitrotoluene are recovered. The product is analyzed by gas chromatography.

The selectivity of the reaction is 72%, the yield of o-nitrophenylethanol is 48% calculated for the amount of o-nitrotoluene introduced.

EXAMPLE 2

A mixture of 137 g (1 mole) of o-nitrotoluene, 120 g of paraformaldehyde, 34 g of potassium hydroxide and 500 ml of dimethyl formamide containing 0.7% by weight of water is stirred at 30° C. for 1.5 hours and then at 55° C. for 1 hour. The reaction mixture is processed as described in Example 1 to obtain 35 g of o-nitrophenylethanol, 20 g of o-nitrotoluene and 35 g of bis-methylol compounds. The bis-methylol compounds were identified by gas chromatographical mass spectrum (GCMS) analysis.

The selectivity of the reaction is 18% for the bis-methylol compounds and 21% for o-nitrophenylethanol.

EXAMPLE 3

A mixture of 137 g (1 mole) of o-nitrotoluene, 130 g of paraformaldehyde, 10 g of potassium hydroxide and 500 ml of dimethyl formamide containing 0.2% by weight of water is stirred at 30° C. for 6 hours. Thereafter the reaction mixture is acidified, filtered, the filtrate is evaporated, and o-nitrotoluene (20 g) is distilled off in vacuo.

190 g of the tris-methylol derivative are obtained, which corresponds to a selectivity of 97.5%. The structure of the product was identified by elementary analysis and GCMS analysis.

EXAMPLE 4

137 g (1 mole) of p-nitrotoluene are treated with the reactants listed in Example 1 under the conditions given in Example 1. 110 g of crude (80% by weight) p-nitrophenylethanol are obtained, and 40 g of p-nitrotoluene are recovered. The crude product is distilled in vacuo to obtain 79 g of the purified substance melting at 61°–63° C. The selectivity of the reaction is 74.5%.

EXAMPLE 5

A mixture of 15.5 g (0.1 moles) of 4-fluoro-2-nitrotoluene, 6 g of paraformaldehyde and 40 ml of dimethyl formamide containing 0.1% by weight of water is heated to 85° C. with stirring, and 4 g of potassium hydroxide covered with 10 ml of dimethyl formamide are added to the mixture at a temperature not exceeding 100° C. Thereafter the mixture is stirred for 5 minutes at a temperature above 85° C., and then the mixture is cooled and filtered. The filtrate is acidified with hydrochloric acid to pH 3, filtered again, and the resulting filtrate is evaporated in vacuo. 17.5 g of a crude product, containing 40% by weight of 2-(o-nitro-p-fluorophenyl)-ethanol and 35% by weight of the starting substance, are obtained.

The selectivity of the reaction is 62.5%. The crude product is subjected to fractional distillation under reduced pressure (13.3 Pa) to obtain 5.3 g of 2-(o-nitro-p-fluorophenyl)-ethanol. The product was identified by GCMS analysis and elementary analysis.

EXAMPLE 6

A mixture of 18.2 g (0.1 moles) of 2,6-dinitrotoluene, 6 g of paraformaldehyde and 40 ml of dimethyl formamide containing 0.9% by weight of water is heated to 60° C. with stirring, and 4 g of potassium hydroxide covered with 10 ml of dimethyl formamide are added to the mixture at a temperature not exceeding 80° C. The resulting mixture is stirred at 70° C. for 5 minutes, thereafter it is processed as described in Example 5. 20 g of a crude product are obtained which contains, as determined by gas chromatography, 25% by weight of 2-(o,o'-dinitrophenyl)-ethanol and 30% by weight of the starting substance.

The selectivity of the reaction is 35%. The crude product is purified by extracting it with water to obtain 5 g of 2-(o,o'-dinitrophenyl)-ethanol. The purity grade of this product is 80%. The product was identified by GCMS analysis.

EXAMPLE 7

16.7 g (0.1 moles) of 3-methyl-4-nitroanisole are hydroxymethylated as described in Example 5. After evaporating the reaction mixture 19 g of a crude product are obtained, which contains, as determined by gas chromatography, 35% by weight of 2-(o-nitro-m-methoxyphenyl)-ethanol and 30% by weight of the starting substance.

The selectivity of the reaction is 51%. The crude product is purified by extracting it with water to obtain 5.5 g of 2-(o-nitro-m-methoxyphenyl)-ethanol with a purity grade of 85%. The product was identified by GCMS analysis.

EXAMPLE 8

15.1 g (0.1 moles) of 3-nitro-o-xylene are hydroxymethylated as described in Example 5. After evaporating the reaction mixture 18 g of a crude product are obtained, which contains, as determined by gas chromatography, 33% by weight of 2-(o-nitro-o'-methylphenyl)-ethanol and 40% by weight of the starting substance.

The selectivity of the reaction is 63%. The crude product is subjected to fractional distillation under reduced pressure (267 Pa) to obtain 4.2 g of 2-(o-nitro-o'-methylphenyl)-ethanol in the temperature range of 140° to 155° C. The purity grade of the product is 90%. The product was identified by GCMS analysis.

EXAMPLE 9

One proceeds as described in Example 1 with the difference that potassium hydroxide is replaced by 28 g of sodium hydroxide. 95 g of 2-(o-nitrophenyl)-ethanol (purity grade: 80%) and 46 g of o-nitrotoluene are obtained.

The selectivity of the reaction is 68.5%. The crude product is subjected to fractional distillation under reduced pressure (267 Pa) to obtain 64 g of 2-(o-nitrophenyl)-ethanol in the temperature range of 125° to 140° C. The purity grade of the product is 96%.

EXAMPLE 10

One proceeds as described in Example 1 with the difference that potassium hydroxide is replaced by a dimethyl formamide solution of 115 g of trimethyl-benzyl-ammonium hydroxide. 110 g of 2-(o-nitrophenyl)-ethanol (purity grade: 80%) and 40 g of o-nitrotoluene are obtained.

The selectivity of the reaction is 74%. The crude product is subjected to fractional distillation as described in Example 9 to obtain 72 g of 2-(o-nitrophenyl)-ethanol with a purity grade of 97%.

EXAMPLE 11

A mixture of 137 g (1 mole) of o-nitrotoluene, 90 g (3 moles) of paraformaldehyde, 28 g of potassium hydroxide and 500 ml of dimethyl formamide containing 0.1% by weight of water is stirred at 35° C. for one hour, thereafter for 10 minutes at 60° C. The reaction mixture is shaken with hexane to separate o-nitrotoluene, weighing 30 g, and o-nitrophenylethanol, weighing 25 g, from the reaction mixture. 60 g of the bis-methylol derivative are obtained as a residue, the purity grade of the bis compound is 80%. The selectivity of the reaction is 31% for the bis derivative.

EXAMPLE 12 (REFERENCE EXAMPLE)

One proceeds as described in Example 1 with the difference that anhydrous dimethyl formamide is used. After processing the reaction mixture 35 g of o-nitrophenylethanol are obtained and 30 g of o-nitrotoluene are recovered.

The selectivity of the reaction is 27%, the yield of o-nitrophenylethanol is 21% calculated for the amount of o-nitrotoluene introduced.

EXAMPLE 13 (REFERENCE EXAMPLE)

One proceeds as described in Example 1 with the difference that dimethyl formamide containing 1.5% by weight of water is used. After processing the reaction mixture 15 g of o-nitrophenylethanol are obtained and 90% of o-nitrotoluene are recovered.

The selectivity of the reaction is 26%, the yield of o-nitrophenylethanol is 8.9% calculated for the amount of o-nitrotoluene introduced.

EXAMPLE 14 (REFERENCE EXAMPLE)

One proceeds as described in Example 1 with the difference that 1 mole (30 g) of paraformaldehyde and 0.3 moles (17 g) of the base are used for 1 mole (137 g) of o-nitrotoluene. 25 g of o-nitrophenylethanol are separated by distillation, and 50 g of o-nitrotoluene are recovered.

The selectivity of the reaction is 23.6%, the yield of o-nitrophenylethanol is 15% calculated for the amount of o-nitrotoluene introduced.

EXAMPLE 15

One proceeds as described in Example 1 with the difference that 2.4 moles (72 g) of paraformaldehyde and 0.8 moles (45 g) of the base are used for 1 mole (137 g) of o-nitrotoluene. 60 g of o-nitrophenylethanol are separated by distillation, no o-nitrotoluene can be recovered.

The selectivity of the reaction is 36%, the yield of o-nitrophenylethanol is 36% calculated for the amount of o-nitrotoluene introduced.

What we claim is:

1. A process for the preparation of a nitrophenylalkanol of the general formula (II),

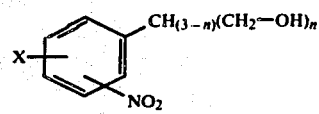

wherein the nitro group is in the ortho or para position, X stands for hydrogen, fluorine or an alkyl, alkoxy or nitro group, and n is 1, 2 or 3, by the selective hydroxymethylation of an ortho- or paranitrotoluene of the general formula (I),

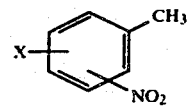

wherein X is as defined above, with an excess of formaldehyde at a temperature above room temperature in dimethyl formamide and in the presence of a strong base, characterized in that the reaction is performed in dimethyl formamide containing 0.1 to 1% by weight of water.

2. A process as claimed in claim 1, characterized in that for the preparation of a monomethylol compound 1 mole of a starting substance of the general formula (I) is reacted with 1.5 to 2.2 moles of formaldehyde and 0.6 to 0.7 moles of a strong base at temperatures above 60° C.

3. A process as claimed in claim 1, characterized in that for the preparation of bis-methylol derivative 1 mole of a starting substance of the general formula (I) is reacted with 3 to 4 moles of formaldehyde and 0.5 to 0.6 moles of a strong base, and the temperature of the reaction mixture is maintained at 30° to 35° C. for at least one hour and thereafter at 50° to 60° C. until the reaction terminates.

4. A process as claimed in claim 1, characterized in that for the preparation of a tris-methylol derivative 1 mole of a starting substance of the general formula (I) is reacted with at least 3 moles of formaldehyde and at most 0.1 moles of a strong base at temperatures below 40° C.

* * * * *